United States Patent [19]

Hansche

[11] Patent Number: Plant 6,671

[45] Date of Patent: Mar. 14, 1989

[54] PEACH TREE CALLED VALLEY RED

[75] Inventor: Paul E. Hansche, Davis, Calif.

[73] Assignee: The Regents of the University of California, Berkeley, Calif.

[21] Appl. No.: 107,140

[22] Filed: Oct. 9, 1987

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Townsend and Townsend

[57] ABSTRACT

A new and distinct dwarf peach cultivar suitable for commercial and/or home garden use. The variety has a unique origin and differs from selections 'Valley Sun' and 'Valley Gem' in that the fruit of this variety is slightly larger than 'Valley Sun' and ripens much earlier than the fruit of selection 'Valley Gem'.

1 Drawing Sheet

DESCRIPTION

This invention relates to a new and distinct variety of dwarf peach tree which resulted from a complex cross, the pedigree of which is set forth below:

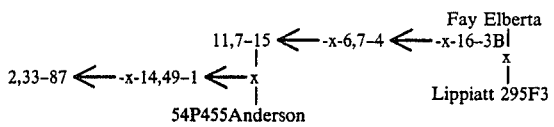

The last step of self pollination of 14,49-1 was made in 1979.

The invention of genotype 'Valley Red' (2, 33-87) was discovered in 1982 and substantially asexually propagated at the University of California, Davis, Calif. Thereafter it was placed in a selection block at the University of California at Davis, and at the Kearney Horticultural Field Station, Fresno County, Calif. and evaluated. The valuation revealed the merit of this new dwarf peach tree and resulted in its selection as a promising cultivar.

Figure 1:
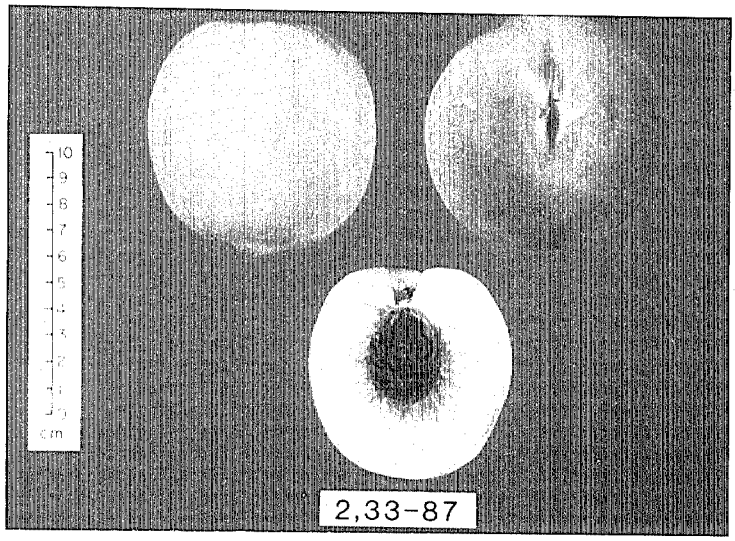
FIG. 1 illustrates peaches of the new cultivar which are typical in size, shape and color.
Figure 2:
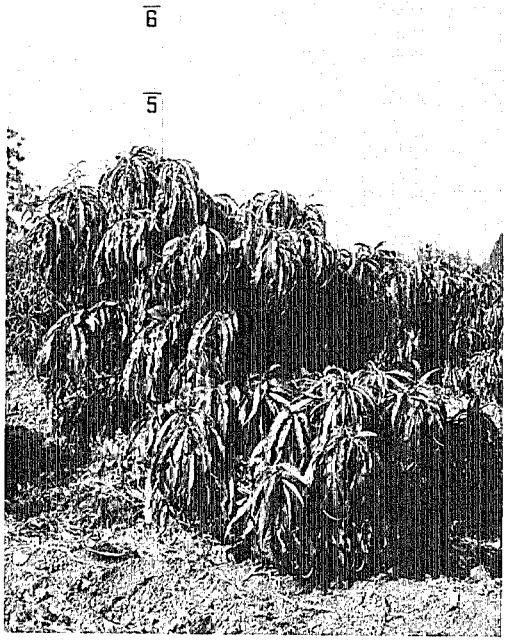
FIG. 2 illustrates a tree of the new cultivar which is typical in size, shape and color.

The characteristics that most distinguish this new dwarf tree from other dwarf freestone peach cultivars are the excellent red blush that covers nearly the entire fruit surface by the time the fruit reaches shipping maturity, and its exceptional firmness.

The fruit of this genotype is of very good eating quality; being sweet, with an excellent flavor. The flesh is a clear yellow color, without any red until near fully ripe.

The characteristics of this new dwarf peach tree, described below in detail, were observed upon its discovery and subsequently through the evaluation period. The color terminology as used herein is in accordance with Nickerson Color Fan, published by Munsell Color Co., 10 East Franklin Street, Baltimore 2, Md.

Tree:

*Genotype.*—Homoszygous dw/dw.

*Size.*—about 5 ft in August of its 6th year at Davis (5–7 ft at maturity) vigorous; shperical. Current seasons shoots — Stout with a leaf internode distance of 6.3±2.0 mm; applegreen, strong greenish yellow 10Y8/11, tinged red where exposed.

*Trunk.*—Little if any trunk.

*Branches.*—Stout, brown to greenish brown (10Y4/3 moderate olive); bark rough; peeling off in recurved platelets which adhere tightly; on younger branches growth cracks longitudinally striated showing light brown beneath (moderate olive brown 2.54).

*Lenticels.*—Moderately numerous, medium size. relatively inconspicuous with low, raised lips.

Leaves: From the middle of shoots 20 to 24 cms long.

*Size.*—Medium; 23±1.5 cm long×3.5±0.5 cm wide.

*Shape.*—Elliptic-lanceolate; base acuminate; apex long, acute-acuminate. Flat to somewhat recurved; apex more or less twisted.

*Blade.*—Thin; dark green above (dark yellowish green 10GY4/5), lighter below. Margin crenate. Midrib sparsely puberulent laterally, next to blade.

*Petiole.*—Short, 1.2+0.18 cm long; moderately thick; channeled on ventral surface; strong yellow green 7.5GY6/8.

*Glands.*—Reniform, usually 8 or more on upper half of the petiole and on the base of the blade.

Flowers: 1–2 per node.

*Corolla.*—Color and surface red (Ox-Blood Red, Plate I) to greenish depending upon exposure; glabrous.

*Calyx lobes.*—Separate; almost conic in shape, apex generally pointed. 4 mm at base by 4 mm long. Lobes reflexed about 90°.

*Petals.*—Showey; broad ovate to nearly round; 15 mm wide×20 mm long to 18 mm wide×18 mm long; clear pink (Rose Pink, Plate XII). Margin more often slightly eroded and/or nicked or slightly cleft at apex, flattish. Claw 1–2 mm medium long; medium stoutness.

Fruit:

*Ripe.*—July 23rd 1983, July 25th in 1984, July 30th in 1985, and July 20th in 1986 at UCD.

*Crop.*—Moderate for tree.

*Size.*—Medium; average weight of fruit 230±19 gms.

*Pubesence.*—Moderate, light.

*Shape.*—Slightly oblong. Length 80±7 mm×cheek dimeter 77±6 mm×suture diameter

78±6 mm Fairly regular, one half often slightly larger, or symmetrical with a somewhat protruding suture lip; apex depressed, or with a short, fleshy tip. Base may slope slightly toward the ventral suture. Axial aspect: Nearly round; the ventral side somewhat thinner than the ventral side. Ventral aspect: Broad elliptic to broad ovate; truncate at base, rounded or truncate at apex; halfs nearly equal to 1 noticeably larger.

*Base.*—Somewhat variable; broad oval in outline. Rather small; flattened at right angles to the fruit axis. Medium shallow depth, conical.

*Sutura.*—The suture edge is smooth, or more commonly somewhat protruding; one-half often somewhat larger and forming a lip.

*Apex.*—The stylar scar, a small dot. Rather deeply creased apically, the crease running somewhat past the stylar scar, to rounded and not at all depressed with the apical point occasionally a low, fleshy tip, sometimes raised.

*Pit cavity.*—Slight.

*Color.*—Ground color a rich, bright golden yellow (strong orange yellow 7.5YR7/11 to moderate orange yellow 7.5YR8/8.

Blush: 80–100% of the fruit is covered with a semi to full deep red (from dark red 2.5R3/7 to strong reddish orange 7.5R5/13).

*Flesh color.*—Medium yellow (firm ripe) to golden yellow (yellow 5 to moderate orange yellow 10YR8/10) when soft ripe. Clear, bright, attractive. No red except for occasional short radiating lines of red near cavity.

*Cavity color.*—Red (dark red 2.5R3/7 to moderate red 2.5R4/10).

*Adhesion.*—Freestone.

*Flesh.*—Medium thick, very firm-melting.

Flavor.—Eating quality very good. Sweet with a mild sub acid flavor (% soluble solids is 13±1.0).

*Stone.*—Medium size; somewhat long elliptic to slightly obovate; moderately plump. The grooves of medium depth and width rounded. Color, dark red brown (moderate brown 5.4R333/3).

*Seed.*—Ovate; moderately plump; testas brown (strong brown 5.4R4/5).

I claim:

1. The new and distinct variety of peach tree herein described and illustrated and identified by the characteristics enumerated above and the parts thereof.

* * * * *